US00PP15405P2

(12) United States Plant Patent
Olesen et al.

(10) Patent No.: US PP15,405 P2
(45) Date of Patent: Dec. 7, 2004

(54) MINIATURE ROSE VARIETY 'POULRA018'

(50) Latin Name: *Rosa hybrida*
Varietal Denomination: POULra018

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 38 days.

(21) Appl. No.: 10/414,520

(22) Filed: Apr. 14, 2003

(51) Int. Cl.[7] ..... A01H 5/00
(52) U.S. Cl. ..... Plt./121
(58) Field of Search ..... Plt./116, 121, 123, Plt./128

*Primary Examiner*—Howard J. Locker

(57) ABSTRACT

A new miniature rose which has abundant, light pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida* 'POULra018'.

SUMMARY OF THE INVENTION

The present discovery constitutes a new and distinct variety of a miniature pot rose plant which was discovered in a cultivated area. The mutation resulted from 'POULra002', a miniature pot rose hybridized by the same inventors. 'POULra002' is described and illustrated in U.S. Plant Pat. No. 13,275, and issued on Nov. 26, 2002. The new rose variety resulted from a naturally occurring mutation of unknown causation on a branch of 'POULra002'.

The rose plant of the present discovery has a unique combination of characteristics which are outstanding in the new variety and which distinguish it from the original rose 'POULra002' as well as all other varieties which we are aware of. For example, the new variety has:

1. Uniform and abundant light pink flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULra018' from all other varieties of which we are aware.

The resulting mutation was selected and evaluations were conducted on the resulting rose plants in a controlled environment.

Asexual reproduction of 'POULra018' by cuttings and traditional budding was first done by L. Pernille and Mogens N. Olesen in their nursery in Fredensborg, Denmark in August 1998. This initial and other subsequent propagations conducted in controlled environments have demonstrated that the characteristics of 'POULra018' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULra018'. Specifically illustrated in FIG. 1:

FIG. 1.1; Stem showing branching and the attachment of leaves, buds, and peduncles;

FIG. 1.2; Flower bud, partially opened bud, and open bloom;

FIG. 1.3; Flower petals, detached;

FIG. 1.4; Sepals, receptacle, and pedicel;

FIG. 1.5; Stem as well as a bare stem exhibiting thorns;

FIG. 1.6; Leaves.

DETAILED DESCRIPTION OF THE VARIETY

The following is a description of 'POULra018', as observed in its growth in a glasshouse in Burlington, Canada. Color references are made using The Royal Horticultural Society (London, England) Colour Chart, 1995, except where common terms of color are used.

For a comparison, several physical characteristics of the rose variety 'POULra001', a rose variety from the same inventors described and illustrated in U.S. Plant Pat. No. 13,487 and issued on Jan. 21, 2003 are compared to 'POULra018' in Chart 1.

CHART 1

| | 'POULra018' | 'POULra001' |
|---|---|---|
| General tonality of open bloom | Red Group 49 C | Red Group 50 D |
| Number of petals | 30 to 35 | 50 to 60 |
| Bloom diameter | 35 mm | 40 to 50 mm |

Classification:
*Botanical.*—*Rosa hybrida.*
*Commercial.*—Miniature.

FLOWER AND FLOWER BUD

Blooming habit: Continuous.

Flower bud:

*Size.*—Upon opening, 20 mm to 25 mm in length from base of receptacle to end of bud.

*Bud form.*—Short, pointed ovoid.

*Bud color.*—As sepals unfold, Red Group 50D; Red Group 50D at ¼ opening.

*Sepals.*—Upper Surface, Green Group 138A to Yellow-Green Group 144B. Lower Surface, Yellow-Green Group 144 A. Weak foliaceous appendages on three of the five sepals. Surfaces of sepals is slightly pubescent. Stipitate glands are located on edges of the sepals. Shape: Sepal apex is cirrose. Base is flat at union with peduncle. Size: 20 to 25 mm long by 5 to 7 mm wide.

*Receptacle.*—Surface: Smooth. Shape: Funnel. Size: 7 mm (h)×8 mm (w). Color: Green Yellow-Green Group 144B.

*Peduncle.*—Surface: Small stipitate glands present. Length: 30 to 37 mm average length. Color: Yellow-Green Group 144B. Strength: Strong.

*Borne.*—Singly.

Flower bloom:

*Fragrance.*—Light floral scent.

*Duration.*—As a pot plant, flowers last from 10 to 14 days.

*Size.*—For a 8–11 cm pot rose, average flower diameter is 35 mm when open.

*Form.*—Shape of flower when viewed from the side: Upon opening, upper part: Convex. Upon opening, lower part: Convex. Open flower, upper part: Flattened convex. Open flower, lower part: Flattened convex.

*Petalage.*—Average range: 30 to 35 petals under normal conditions with 4 to 6 petaloids.

Color:

*Upon opening, petals.*—Outermost petals: Outer Side: Red Group 55 C. Inner Side: Red Group 49 D. Innermost petals: Outer Side: Red Group 55 C. Inner Side: Red Group 49 D.

*Upon opening, basal petal spots.*—Outermost petals: Outer Side: Green-Yellow 1 D. Inner Side: Green-Yellow 1 D. Innermost petals: Outer Side: Green-Yellow 1 D. Inner Side: Green-Yellow 1 D.

*After opening, petals.*—Outermost petals: Outer Side: Red Group 55 C. Inner Side: Red Group 49 D. Innermost petals: Outer Side: Red Group 55 C. Inner Side: Red Group 49 D.

*After opening, basal petal spots.*—Outermost petals: Outer Side: Green-Yellow 1 D. Inner Side: Green-Yellow 1 D. Innermost petals: Outer Side: Green-Yellow 1 D. Inner Side: Green-Yellow 1 D.

General tonality: On open flower Red Group 49C. No change in the general tonality at the end of the 9th day. Afterwards, general tonality is Red Group 49D.

Petals:

*Petal reflex.*—Somewhat.

*Petal edge.*—Entire.

*Apex shape.*—Deltoid.

*Base shape.*—Acute.

*Petaloids.*—Quantity: 4 to 6. Size: 6 mm long; 5 mm wide. Color: Red Group 55 D.

*Thickness.*—Thin.

*Arrangement.*—Formal.

Reproductive organs:

*Pollen.*—Color: Yellow-Orange Group 14 B. Quantity: Average.

*Anthers.*—Size: 1 mm long. Color: Yellow-Orange Group 22A. Quantity: 24.

*Filaments.*—Color: Green-Yellow Group 1A. Length: 7 to 8 mm.

*Stigmas.*—Slightly inferior in location to anthers. Color: Greyed-Green Group 196D.

*Styles.*—Color: Greyed-Green Group 196D.

*Seed formation.*—Hips: None observed.

PLANT

Plant growth: Vigorous, compact, upright to bushy. When grown as a 8–11 cm pot plant, the average height of the plant itself is 20 cm and the average width is 20 cm.

Stems:

*Color.*—Young wood: Yellow-Green Group 144B. Older wood: Yellow-Green Group 144A.

*Prickles.*—Incidence: No thorns observed.

*Surface.*—Young wood: Smooth. Older wood: Smooth.

Plant foliage: Normal number of leaflets on normal leaves in middle of the stem: 5 leaflets.

*Leaf size.*—85 mm (l)×55 mm (w).

*Quantity.*—Average.

*Color.*—Mature foliage: Upper Leaf Surface: Green Group 137A. Lower Leaf Surface: Green Group 138B. Juvenile foliage: Upper Leaf Surface: Yellow-Green Group 144 A. Lower Leaf Surface: Green Group 138B. Anthocyanin intonation: Location: On plants grown under high light conditions, leaf margins may exhibit intonations of Greyed-Red Group 181 A.

Plant leaves and leaflets:

*Stipules.*—Size: 8 mm in length. Color: Yellow-Green Group 144B. changing to Green Group 137A at the apex. Stipitate glands: Present at stipule edges. Anthocyanin: Greyed-Red Group 181A.

*Petiole.*—Length: 10 mm. Color: Yellow-Green Group 144B changing to Greyed-Red Group 181 A.

*Rachis.*—Color: Yellow-Green Group 144B with intonations of Greyed-Red Group 181A.

*Leaflet.*—Edge: Finely serrated. Shape: Ovate. Texture: Matte Finish. Thickness: Thin. Arrangement: Odd pinnate. Venation: Reticulate.

Disease resistance: Average resistance to mildew, black spot, and *Botrytis* under normal growing conditions in Burlington, Canada and in Fredensborg, Denmark.

It is claimed:

1. A new and distinct variety of rose of the miniature class, substantially as herein illustrated and described as a distinct and novel rose variety due to its abundant, light pink flowers, vigorous growth, compact habit, suitability for production from softwood cuttings in pots, and durable flowers and foliage which make the variety suitable for distribution in the floral industry.

* * * * *

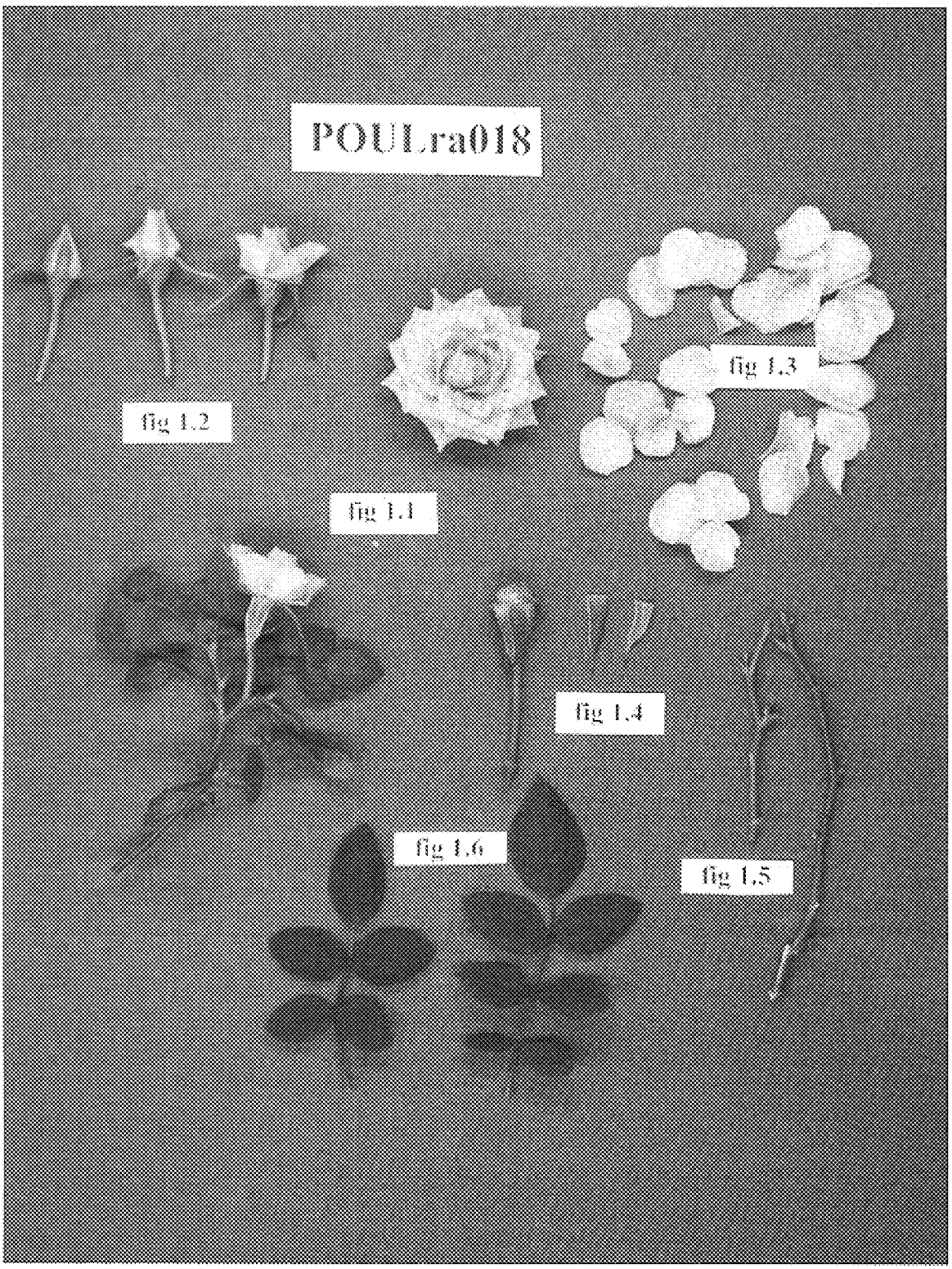
POULra018
fig 1.2
fig 1.1
fig 1.3
fig 1.4
fig 1.6
fig 1.5